(12) United States Patent
Cerretti

(10) Patent No.: US 6,194,172 B1
(45) Date of Patent: Feb. 27, 2001

(54) CYTOKINE DESIGNATED LERK-6

(75) Inventor: Douglas P. Cerretti, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/173,492

(22) Filed: Oct. 15, 1998

Related U.S. Application Data

(60) Division of application No. 08/920,440, filed on Aug. 29, 1997, now Pat. No. 5,919,305, which is a continuation-in-part of application No. 08/538,709, filed on Oct. 3, 1995, which is a continuation-in-part of application No. 08/318,393, filed on Oct. 5, 1994, now abandoned.

(51) Int. Cl.$^7$ ............................. C12N 15/00; C12N 15/09
(52) U.S. Cl. ................. 435/69.1; 435/252.3; 435/320.1; 435/69.5; 536/23.5
(58) Field of Search .................................. 435/69.1, 69.5, 435/252.3, 320.1; 536/23.5

(56) References Cited

U.S. PATENT DOCUMENTS

| | | | |
|---|---|---|---|
| 5,457,048 | * 10/1995 | Pasquale et al. | ..................... 536/23.5 |
| 5,512,457 | * 4/1996 | Lyman et al. | ......................... 536/23.5 |
| 5,516,658 | * 5/1996 | Beckmann et al. | ................. 536/23.5 |

FOREIGN PATENT DOCUMENTS

| | | |
|---|---|---|
| WO 96/09384 | 3/1996 | (WO) . |
| WO 96/10911 | 4/1996 | (WO) . |
| WO 96/17925 | 6/1996 | (WO) . |
| 9623000 | * 8/1996 | (WO) . |

OTHER PUBLICATIONS

Kozlosky, Carl J. et al., "Ligands for the receptor tyrosine kinases hek and elk: isolation of cDNAs encoding a family of proteins," *Oncogene*, 10 (2):299–306, Jan. 19, 1995.

Beckmann, M. P. et al., "Molecular characterization of a family of ligands for eph–related tyrosine kinase receptors", *EMBO Journal 13*: 3757–3762, 1994.*

Carpenter, M.K., et al., "Ligands for EPH–Related Tyrosine Kinase Receptors are Developmentally Regulated in the CNS", *Journal of Neuroscience Research 42*: 199–206, 1995.*

Cheng, H., et al., "Identification and Cloning of ELF–1, a Developmentally–Expressed Ligand for the Mek4 and Sek Receptor Tyrosine Kinases", *Manuscript for Dept. of Cell Biology*, Harvard Medical School: 36 pages, Sep. 16, 1994.*

Cheng, H., et al., "Identification and Cloning of ELF–1, A Developmentally–Expressed Ligand for the Mek4 and Sek Receptor Tyrosine Kinases", *Cell 79*: 157–168, 1994.*

Shao, H., et al., "DNA Cloning and Characterization of a Cek7 Receptor Protein–tyrosine Kinase Ligand That is Identical to the Ligand (ELF–1) for the Mek–4 and Sek Receptor Protein–tyrosine Kinases", *J. Biological Chemistry 270(8)*: 3467–70, 1995.*

Drescher et al., *Cell 82*: p. 359–70 (abstract only) 1995.*

Wicks, I.P., et al., "Molecular cloning of HEK, the gene encoding a receptor tyrosine kinase expressed by human lymphoid tumor cell lines", *Proc. Natl. Acad. Sci. 89*: 1611–15, 1992.*

Lhotak, V., et al., "Characterization of Elk, a Brain–Specific Receptor Tyrosine Kinase", *Molecular and Cellular Biology 11*: 2496–2502, 1991.

Tuzi, N.L., et al., "eph, the largest known family of putative growth factor receptors", *Br. J. Cancer 69*: 417–21, 1994.

Pandey, A., et al., "Receptor orphans find a family", *Current Biology 5 (9)*: 986–89, 1995.

Frömmel, C., et al., "An Estimate on the Effect of Point Mutation and Natural Selection on the Rate of Amino Acid Replacement in Proteins", *Journal of Molecular Evolution 21*: 233–57, 1985.

Bowie, J., et al., "Deciphering the Message in Protein Sequences: Tolerance to Amino Acid Substitutions" *Science 247*: 1306–10, 1990.

"The Protein Folding Problem and Tertiary Structure Prediction", ed. Merz, 1994 p. 433–43

Aasheim, H.C., et al., "Cloning, Chromosal Mapping, and Tissue Expression of the Gene Encoding the Human Eph–Family Kinase Ligand Ephrin–A2," *Biochem Biophys Res Commun 252(2)*:378–383, 1998.

* cited by examiner

*Primary Examiner*—Garnette D. Draper
(74) *Attorney, Agent, or Firm*—Sughrue, Mion, Zinn, Macpeak & Seas, PLLC

(57) ABSTRACT

The invention is directed to LERK-6 as a purified and isolated protein, the DNA encoding the LERK-6, host cells transfected with cDNAs encoding LERK-6.

32 Claims, No Drawings

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: LERK-6

(ix) FEATURE:
        (A) NAME/KEY: CDS
        (B) LOCATION: 1..552

(xi) SEQUENCE DESCRIPTION: SEQ ID NO:1:

```
GCC CGG GCC AAC GCT GAC CGA TAC GCA GTC TAC TGG AAC CGT AGC AAC        48
Ala Arg Ala Asn Ala Asp Arg Tyr Ala Val Tyr Trp Asn Arg Ser Asn
 1               5                  10                  15

CCC AGG TTT CAG GTG AGC GCT GTG GGT GAT GGC GGC GGC TAT ACC GTG        96
Pro Arg Phe Gln Val Ser Ala Val Gly Asp Gly Gly Gly Tyr Thr Val
                20                  25                  30

GAG GTG AGC ATC AAC GAC TAC CTG GAT ATC TAC TGC CCA CAC TAC GGG       144
Glu Val Ser Ile Asn Asp Tyr Leu Asp Ile Tyr Cys Pro His Tyr Gly
             35                  40                  45

GCG CCG CTG CCC CCG GCT GAG CGC ATG GAG CGG TAC ATC CTG TAC ATG       192
Ala Pro Leu Pro Pro Ala Glu Arg Met Glu Arg Tyr Ile Leu Tyr Met
         50                  55                  60

GTG AAT GGT GAG GGC CAC GCC TCC TGT GAC CAC CGG CAG CGA GGC TTC       240
Val Asn Gly Glu Gly His Ala Ser Cys Asp His Arg Gln Arg Gly Phe
 65                  70                  75                  80

AAG CGC TGG GAA TGC AAC CGG CCC GCA GCG CCC GGG GGA CCC CTC AAG       288
Lys Arg Trp Glu Cys Asn Arg Pro Ala Ala Pro Gly Gly Pro Leu Lys
                 85                  90                  95

TTC TCA GAG AAG TTC CAA CTC TTC ACC CCC TTT TCC CTG GGC TTT GAG       336
Phe Ser Glu Lys Phe Gln Leu Phe Thr Pro Phe Ser Leu Gly Phe Glu
                100                 105                 110

TTC CGG CCT GGC CAC GAA TAC TAC TAC ATC TCT GCC ACA CCT CCC AAC       384
Phe Arg Pro Gly His Glu Tyr Tyr Tyr Ile Ser Ala Thr Pro Pro Asn
            115                 120                 125

CTC GTG GAC CGA CCC TGC CTG CGA CTC AAG GTT TAT GTG CGT CCA ACC       432
Leu Val Asp Arg Pro Cys Leu Arg Leu Lys Val Tyr Val Arg Pro Thr
        130                 135                 140

AAT GAG ACC CTG TAT GAG GCT CCA GAG CCC ATC TTC ACC AGT AAC AGC       480
Asn Glu Thr Leu Tyr Glu Ala Pro Glu Pro Ile Phe Thr Ser Asn Ser
145                 150                 155                 160
```

```
TCC TGC AGC GGC CTG GGT GGC TGC CAC CTC TTC CTC ACC ACC GTC CCT    528
Ser Cys Ser Gly Leu Gly Gly Cys His Leu Phe Leu Thr Thr Val Pro
            165                 170                 175

GTG CTG TGG TCC CTT CTG GGC TCC TAG                                555
Val Leu Trp Ser Leu Leu Gly Ser
            180
```

(2) INFORMATION FOR SEQ ID NO:2:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Arg Ala Asn Ala Asp Arg Tyr Ala Val Tyr Trp Asn Arg Ser Asn
 1               5                  10                  15

Pro Arg Phe Gln Val Ser Ala Val Gly Asp Gly Gly Tyr Thr Val
            20                  25                  30

Glu Val Ser Ile Asn Asp Tyr Leu Asp Ile Tyr Cys Pro His Tyr Gly
            35                  40                  45

Ala Pro Leu Pro Pro Ala Glu Arg Met Glu Arg Tyr Ile Leu Tyr Met
 50                  55                  60

Val Asn Gly Glu Gly His Ala Ser Cys Asp His Arg Gln Arg Gly Phe
65                  70                  75                  80

Lys Arg Trp Glu Cys Asn Arg Pro Ala Ala Pro Gly Gly Pro Leu Lys
            85                  90                  95

Phe Ser Glu Lys Phe Gln Leu Phe Thr Pro Phe Ser Leu Gly Phe Glu
            100                 105                 110

Phe Arg Pro Gly His Glu Tyr Tyr Tyr Ile Ser Ala Thr Pro Pro Asn
            115                 120                 125

Leu Val Asp Arg Pro Cys Leu Arg Leu Lys Val Tyr Val Arg Pro Thr
130                 135                 140

Asn Glu Thr Leu Tyr Glu Ala Pro Glu Pro Ile Phe Thr Ser Asn Ser
145                 150                 155                 160

Ser Cys Ser Gly Leu Gly Gly Cys His Leu Phe Leu Thr Thr Val Pro
            165                 170                 175

Val Leu Trp Ser Leu Leu Gly Ser
            180
```

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GATATTTACT GCCCGCACTA CAACAGCT                                     28
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

AGAGAAGGCG CTGTAGCGCT GGAAC                                            25

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

ACGTAGTCTA CTGGAACTCC AGTAACCCCA G                                     31

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

AGCCTCAAGC ACTGGCCAGA ACTCTCTCTG GAGT                                  34

(2) INFORMATION FOR SEQ ID NO:7:

(i) SEQUENCE CHARACTERISTICS:
        (A) LENGTH: 314 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 2..313

(xi) SEQUENCE DESCRIPTION: SEQ ID NO:7:

G TTC CAC GCA GGC GCG GGG GAC GAC GGC GGG GGC TAC ACG GTG GAG          46
  Phe His Ala Gly Ala Gly Asp Asp Gly Gly Gly Tyr Thr Val Glu
   1               5                  10                  15

GTG AGC ATC AAT GAC TAC CTG GAC ATC TAC TGC CCG CAC TAT GGG GCG        94
Val Ser Ile Asn Asp Tyr Leu Asp Ile Tyr Cys Pro His Tyr Gly Ala
             20                  25                  30

```
CCG CTG CCG CCG GCC GAG CGC ATG GAG CAC TAC GTG CTG TAC ATG GTC    142
Pro Leu Pro Pro Ala Glu Arg Met Glu His Tyr Val Leu Tyr Met Val
            35                  40                  45

AAC GGC GAG GGC CAC GCC TCC TGC GAC CAC CGC CAG CGC GGC TTC AAG    190
Asn Gly Glu Gly His Ala Ser Cys Asp His Arg Gln Arg Gly Phe Lys
            50                  55                  60

CGC TGG GAG TGC AAC CGG CCC GCG GCG CCC GGG GGG CCG CTC AAG TTC    238
Arg Trp Glu Cys Asn Arg Pro Ala Ala Pro Gly Gly Pro Leu Lys Phe
 65                  70                  75

TCG GAG AAG TTC CAG CTC TTC ACG CCC TTC TCC CTG GGC TTC GAG TTC    286
Ser Glu Lys Phe Gln Leu Phe Thr Pro Phe Ser Leu Gly Phe Glu Phe
 80                  85                  90                  95

CGG CCC GGC CAC GAG TAT TAC TAC ATC T                              314
Arg Pro Gly His Glu Tyr Tyr Tyr Ile
                100
```

(2) INFORMATION FOR SEQ ID NO:8:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:8:

```
Phe His Ala Gly Ala Gly Asp Asp Gly Gly Gly Tyr Thr Val Glu Val
 1               5                  10                  15

Ser Ile Asn Asp Tyr Leu Asp Ile Tyr Cys Pro His Tyr Gly Ala Pro
            20                  25                  30

Leu Pro Pro Ala Glu Arg Met Glu His Tyr Val Leu Tyr Met Val Asn
            35                  40                  45

Gly Glu Gly His Ala Ser Cys Asp His Arg Gln Arg Gly Phe Lys Arg
            50                  55                  60

Trp Glu Cys Asn Arg Pro Ala Ala Pro Gly Gly Pro Leu Lys Phe Ser
 65                  70                  75                  80

Glu Lys Phe Gln Leu Phe Thr Pro Phe Ser Leu Gly Phe Glu Phe Arg
                85                  90                  95

Pro Gly His Glu Tyr Tyr Tyr Ile
            100
```

(2) INFORMATION FOR SEQ ID NO:9:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 1I642
        (A) NAME/KEY: Signal Peptide
        (B) LOCATION: 1-90

(xi) SEQUENCE DESCRIPTION: SEQ ID NO:9:

```
ATG GCG CCC GCG CAG CGC CCG CTG CTC CCG CTG CTG CTC CTG CTG TTA    48
Met Ala Pro Ala Gln Arg Pro Leu Leu Pro Leu Leu Leu Leu Leu Leu
            -25                 -20                 -15
```

```
CCG CTG CCG CCG CCG CCC TTC GCG CGC GCC GAG GAC GCC GCC CGC GCC      96
Pro Leu Pro Pro Pro Pro Phe Ala Arg Ala Glu Asp Ala Ala Arg Ala
        -10                 -5                   1

AAC TCG GAC CGC TAC GCC GTC TAC TGG AAC CGC AGC AAC CCC AGG TTC     144
Asn Ser Asp Arg Tyr Ala Val Tyr Trp Asn Arg Ser Asn Pro Arg Phe
     5                  10                  15

CAC GCA GGC GCG GGG GAC GAC GGC GGG GGC TAC ACG GTG GAG GTG AGC     192
His Ala Gly Ala Gly Asp Asp Gly Gly Gly Tyr Thr Val Glu Val Ser
 20              25                  30                      35

ATC AAT GAC TAC CTG GAC ATC TAC TGC CCG CAC TAT GGG GCG CCG CTG     240
Ile Asn Asp Tyr Leu Asp Ile Tyr Cys Pro His Tyr Gly Ala Pro Leu
                 40                  45                  50

CCG CCG GCC GAG CGC ATG GAG CAC TAC GTG CTG TAC ATG GTC AAC GGC     288
Pro Pro Ala Glu Arg Met Glu His Tyr Val Leu Tyr Met Val Asn Gly
             55                  60                  65

GAG GGC CAC GCC TCC TGC GAC CAC CGC CAG CGC GGC TTC AAG CGC TGG     336
Glu Gly His Ala Ser Cys Asp His Arg Gln Arg Gly Phe Lys Arg Trp
         70                  75                  80

GAG TGC AAC CGG CCC GCG GCG CCC GGG GGG CCG CTC AAG TTC TCG GAG     384
Glu Cys Asn Arg Pro Ala Ala Pro Gly Gly Pro Leu Lys Phe Ser Glu
     85                  90                  95

AAG TTC CAG CTC TTC ACG CCC TTC TCC CTG GGC TTC GAG TTC CGG CCC     432
Lys Phe Gln Leu Phe Thr Pro Phe Ser Leu Gly Phe Glu Phe Arg Pro
100                 105                 110                 115

GGC CAC GAG TAT TAC TAC ATC TCT GCC ACG CCT CCC AAT GCT GTG GAC     480
Gly His Glu Tyr Tyr Tyr Ile Ser Ala Thr Pro Pro Asn Ala Val Asp
                120                 125                 130

CGG CCC TGC CTG CGA CTG AAG GTG TAC GTG CGG CCG ACC AAC GAG ACC     528
Arg Pro Cys Leu Arg Leu Lys Val Tyr Val Arg Pro Thr Asn Glu Thr
            135                 140                 145

CTG TAC GAG GCT CCT GAG CCC ATC TTC ACC AGC AAT AAC TCG TGT AGC     576
Leu Tyr Glu Ala Pro Glu Pro Ile Phe Thr Ser Asn Asn Ser Cys Ser
        150                 155                 160

AGC CCG GGC GGC TGC CGC CTC TTC CTC AGC ACC ATC CCC GTG CTC TGG     624
Ser Pro Gly Gly Cys Arg Leu Phe Leu Ser Thr Ile Pro Val Leu Trp
    165                 170                 175

ACC CTC CTG GGT TCC TAG                                             642
Thr Leu Leu Gly Ser *
180
```

(2) INFORMATION FOR SEQ ID NO:10:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Pro Ala Gln Arg Pro Leu Leu Pro Leu Leu Leu Leu Leu Leu
            -25                 -20                 -15

Pro Leu Pro Pro Pro Pro Phe Ala Arg Ala Glu Asp Ala Ala Arg Ala
        -10                 -5                   1

Asn Ser Asp Arg Tyr Ala Val Tyr Trp Asn Arg Ser Asn Pro Arg Phe
     5                  10                  15

His Ala Gly Ala Gly Asp Asp Gly Gly Gly Tyr Thr Val Glu Val Ser
 20              25                  30                      35

Ile Asn Asp Tyr Leu Asp Ile Tyr Cys Pro His Tyr Gly Ala Pro Leu
                 40                  45                  50
```

-continued

```
Pro Pro Ala Glu Arg Met Glu His Tyr Val Leu Tyr Met Val Asn Gly
            55              60              65

Glu Gly His Ala Ser Cys Asp His Arg Gln Arg Gly Phe Lys Arg Trp
        70              75              80

Glu Cys Asn Arg Pro Ala Ala Pro Gly Gly Pro Leu Lys Phe Ser Glu
    85              90              95

Lys Phe Gln Leu Phe Thr Pro Phe Ser Leu Gly Phe Glu Phe Arg Pro
100             105             110             115

Gly His Glu Tyr Tyr Tyr Ile Ser Ala Thr Pro Pro Asn Ala Val Asp
                120             125             130

Arg Pro Cys Leu Arg Leu Lys Val Tyr Val Arg Pro Thr Asn Glu Thr
            135             140             145

Leu Tyr Glu Ala Pro Glu Pro Ile Phe Thr Ser Asn Asn Ser Cys Ser
        150             155             160

Ser Pro Gly Gly Cys Arg Leu Phe Leu Ser Thr Ile Pro Val Leu Trp
    165             170             175

Thr Leu Leu Gly Ser
180
```

CYTOKINE DESIGNATED LERK-6

RELATED U.S. APPLICATION DATA

This is a divisional of U.S. Ser. No. 08/920,440, filed Aug. 29, 1997, now U.S. Pat. No. 5,919,905 continuation-in-part of U.S. Ser. No. 08/538,709, filed Oct. 3, 1995, currently pending, which is a continuation-in-part of U.S. Ser. No. 08/318,393, filed Oct. 5, 1994 now abandoned.

FIELD OF THE INVENTION

The present invention relates to cytokine polypeptides designated as LERK-6 that bind to the hek or elk receptor, the nucleic acids encoding such polypeptides, processes for production of recombinant LERK-6 polypeptides, and pharmaceutical compositions containing such polypeptides.

BACKGROUND OF THE INVENTION

Proteins known as the receptor tyrosine kinases have an intrinsic kinase activity that is activated upon ligand binding. This class of proteins is characterized by conserved structural motifs within the catalytic domains (Hanks et al., *Science*, 242:42, 1988) and can be subdivided into families based on structural features of the regions N-terminal to the catalytic domain.

Boyd et al. (*J. Biol. Chem.*, 267:3262, 1992) purified a cell-surface glycoprotein exhibiting tyrosine kinase activity. The amino acid sequence identified this protein as a member of the eph/elk family, and the protein was thus designated hek (human eph/elk-like kinase). A monoclonal antibody immunoreactive with hek was used to study hek expression on a number of human cell types (Boyd et al., supra). Hek antigen was detected on the human pre-B cell leukemia cell line LK63 (the cell line employed as the immunogen against which the antibody was raised) and the human T-cell leukemia cell line, JM. The Raji B lymphoma cell line showed weak hek antigen expression, and the remaining cell lines tested (both normal and tumor cell lines, among which were hemopoietic cell lines that included pre-B and T-cell lines) were consistently negative. Of the normal and tumor tissue biopsy specimens that were also tested for hek antigen expression, none of the normal tissues was positive and only a very low proportion of hemopoietic tumors was positive.

Expression of hek transcripts in the above-described LK63 and JM cell lines, as well as the human T-cell leukemia cell line HSB-2, has been demonstrated by northern blot analysis (Wicks et al., *Proc. Natl. Acad. Sci. USA*, 89:1611, 1992). Nucleotide and amino acid sequences for an isolated hek cDNA clone are presented in Wicks et al., supra.

The cell surface protein designated elk is another member of the eph-related tyrosine kinase receptor family of proteins. A partial clone of elk was first discovered in a rat brain cDNA expression library that was screened for proteins expressing tyrosine kinase activity (Letwin et al., *Oncogene* 3:621, 1988). Later, a composite sequence spanning the entire elk coding region was derived from partial clones isolated from a rat brain cDNA library and a rat cerebellar brain library using the partial clone as a probe (Lhotak et al., *Mol. Cell. Biol.* 11:2496, 1991).

The hek and elk proteins are closely related to a number of other receptor tyrosine kinases, including the hek homologs mek4 and cek4 (Sajjadi et al. *New Biol.* 3:769, 1991); eek (Chan et al. *Oncogene* 6:1057, 1991); erk (Chan et al. supra.), eck (Lindberg et al. *Mol. Cell. Biol.* 10:6316, 1990); cek5 (Pasquale, E. B. *Cell Regulation* 2:523, 1991); and eph (Hirai et al. *Science* 238:1717, 1987). The proteins of this subfamily are related not only in their cytoplasmic domains, but also in their extracellular domains, which are 41 to 68% identical. Interestingly, the tissue distributions of these various receptors are diverse. For example, expression of elk mRNA has been reported to be limited to testis and brain (Lhotak et al., supra), whereas eck is found not only in these same two tissues but in lung, intestine, kidney, spleen, ovary, and skin as well. In addition, most eph-related receptors are primarily expressed in the brain. Due to the homology of the receptors in the eph family, a given ligand for one specific receptor may also bind other receptors.

Those ligands that have been identified for the receptor tyrosine kinases are a diverse group of proteins that affect the growth, differentiation, and survival of cells expressing the receptors. Ligands for hek and elk have been isolated, as discussed in more detail below.

Identification of additional ligands for hek and elk that may exist would prove useful in investigating the nature of cellular processes regulated by signaling through these receptors. If enhancement or inhibition of a particular biological signal mediated through these receptors is desired, it is advantageous to identify each of the proteins that may play a role in transduction of such signals. Further, it is known that certain proteins can bind to receptors without initiating signal transduction, including interleukin-1 receptor antagonist protein (Eisenberg et al., *Nature* 343:341, 1990; Hannum et al., *Nature* 343:336, 1990; and Carter et al., *Nature* 344:633, 1990). Identification of additional proteins that bind hek or elk is also desirable in order to determine whether such proteins function as antagonists.

SUMMARY OF THE INVENTION

The present invention pertains to mammalian LERK-6 as an isolated or homogeneous protein. In addition, the invention is directed to isolated DNAs encoding mammalian LERK-6 and to expression vectors comprising a cDNA encoding mammalian LERK-6. Within the scope of this invention are host cells that have been transfected or transformed with expression vectors that comprise a cDNA encoding LERK-6, and processes for producing LERK-6 by culturing such host cells under conditions conducive to expression of LERK-6.

In addition, LERK-6 can be bound to a solid phase matrix and used to affinity-purify or separate cells that express hek or elk on their cell surface. The invention encompasses separating cells having the hek or elk receptor on the surface thereof from a mixture of cells in solution, comprising contacting the cells in the mixture with a contacting surface having a LERK-6 molecule thereon, and separating the contacting surface and the solution.

DETAILED DESCRIPTION OF THE INVENTION

A cDNA encoding murine LERK-6 has been isolated and is disclosed in SEQ ID NO:1. An exon from the human LERK-6 has been isolated and is disclosed in SEQ ID NO:7. DNA encoding a full length human LERK-6 has been isolated and is disclosed in SEQ ID NO:9. This discovery of a cDNA encoding LERK-6 enables construction of expression vectors comprising cDNAs encoding LERK-6; host cells transfected or transformed with the expression vectors; biologically active LERK-6 as homogeneous proteins; and antibodies immunoreactive with LERK-6.

LERK-6 may be useful in the enhancement, stimulation, proliferation or growth of cells expressing the hek or elk receptor. Since the hek or elk receptor is found in the tissue of the brain and testis, treatment of a variety of conditions associated with tissue damage thereof is possible. Moreover, the ligand and receptor complex may be involved in neural growth, development and/or maintenance. While not limited to such, particular uses of the LERK-6 are described infra.

As used herein, the term "LERK-6" refers to a genus of polypeptides that bind and complex independently with hek or elk receptor found on T-cells and brain cells. The term "LERK-6" encompasses polypeptides having the amino acid sequence 1–184 of SEQ ID NO:2, proteins that are encoded by nucleic acids that contain the nucleic acid sequence of SEQ ID NO:7, and polypeptides having the amino acid sequence 1–184 of SEQ ID NO:10. In addition, LERK-6 encompasses polypeptides that have a high degree of similarity or a high degree of identity with the amino acid sequence 1–184 of SEQ ID NO:2, the amino acid sequence of SEQ ID NO:8, and amino acids 1–184 of SEQ ID NO:10, and which polypeptides are biologically active and bind the hek or elk receptor. In addition, the term "murine LERK-6" refers to biologically active gene products of the DNA of SEQ ID NO:1 and the term "human LERK-6 refers to biologically active gene products of the DNA of SEQ ID NO:9. Further encompassed by the term "LERK-6" are the GPI-linked proteins (which include an extracellular region and a C-terminal hydrophobic region), and soluble or truncated proteins that comprise primarily the receptor-binding portion of the protein, retain biological activity and are capable of being secreted. Specific examples of such soluble proteins are those comprising the sequence of amino acids 1 (Ala)–145 (Asn) of SEQ ID NO:2 and those comprising the sequence of amino acids 1–145 of SEQ ID NO:10.

The term "hek/elk" means either hek or elk or both hek and elk. For example, the term "anti-hek/elk antibodies" refers to antibodies against either hek or elk. The term "hek/elk-expressing cells" refers to cells that express either the hek receptor or the elk receptor, or cells that express both the hek and elk receptors.

The term "biologically active" as it refers to LERK-6, means that the LERK-6 is capable of binding to hek/elk.

"Isolated" means that LERK-6 is free of association with other proteins or polypeptides, for example, as a purification product of recombinant host cell culture or as a purified extract.

A "LERK-6 variant" as referred to herein, means a polypeptide substantially homologous to native LERK-6, but which has an amino acid sequence different from that of native LERK-6 (human, murine or other mammalian species) because of one or more deletions, insertions or substitutions. The variant amino acid sequence preferably is at least 80% identical to a native LERK-6 amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring LERK-6 variants or alleles are also encompassed by the invention. Examples of such variants are proteins that result from alternate mRNA splicing events or from proteolytic cleavage of the LERK-6 protein, wherein the LERK-6 binding property is retained. Alternate splicing of mRNA may yield a truncated but biologically active LERK-6 protein, such as a naturally occurring soluble form of the protein, for example. Variations attributable to proteolysis include, for example, differences in the N- or C-termini upon expression in different types of host cells, due to proteolytic removal of one or more terminal amino acids from the LERK-6 protein (generally from 1–5 terminal amino acids).

LERK-6 is predicted to be anchored to the cell surface via glycosyl-phosphatidylinositol (GPI) linkage. GPI membrane anchors, including the chemical structure and processing thereof, are described in Ferouson, M. and Williams, A., *Ann. Rev. Biochem.,* 57:285, 1988 (hereby incorporated by reference). When initially expressed, certain proteins comprise a C-terminal hydrophobic domain that contains signals for GPI anchoring. A cleavage site is located upstream, often about 10–12 amino acids upstream of the N-terminus of the hydrophobic domain. Post translational processing includes cleavage of the protein at this cleavage site. A GPI anchor attaches to the newly exposed C-terminal amino acid of the processed, mature protein. Thus, when LERK-6 proteins are expressed in cells that recognize GPI anchoring signals in the hydrophobic domain, the full length amino acid sequence of SEQ ID NO:2 and SEQ ID NO:10 represents precursor forms of the proteins.

Based on consensus sequences derived from other GPI-anchored proteins, the hydrophobic region in LERK-6 of the present invention likely is between and includes, amino acids 170 (Leu) and 184 (Ser) of SEQ ID NO:2 and SEQ ID NO:10. Between the hydrophobic domain and the receptor-binding domain, is a spacer region of about 22 to 25 amino acids in length. The spacer region extends from approximately amino acid 145 (Asn), 146 (Glu) or 147 (Thr) to about amino acid 169 (His) of SEQ ID NO:2 and SEQ ID NO:10

Example 3 describes the construction of a novel hek:Fc fusion protein that may be utilized in the screening for LERK-6. Other antibody Fc regions may be substituted for the human IgG1 Fc region described in the Example. Other suitable Fc regions are those that can bind with high affinity to protein A or protein G, and include the Fc region of human IgG1 or fragments of the human or murine IgG1 Fc region, e.g., fragments comprising at least the hinge region so that interchain disulfide bonds will form. The hek:Fc fusion protein offers the advantage of being easily purified. In addition, disulfide bonds form between the Fc regions of two separate fusion protein chains, creating dimers.

As described supra, an aspect of the invention is soluble LERK-6 polypeptides. Soluble LERK-6 polypeptides comprise all or part of the extracellular domain of a native LERK-6 but lack the GPI signal that would cause retention of the polypeptide on a cell membrane. Soluble LERK-6 polypeptides advantageously comprise the native (or a heterologous) signal peptide when initially synthesized to promote secretion, but the signal peptide is cleaved upon secretion of LERK-6 from the cell. Soluble LERK-6 polypeptides encompassed by the invention retain the ability to bind the hek or elk receptor. Indeed, soluble LERK-6 may also include part of the GPI signal or part of the cytoplasmic domain or other sequences, provided that the soluble LERK-6 protein can be secreted.

Soluble LERK-6 may be identified (and distinguished from its non-soluble membrane-bound counterparts) by separating intact cells which express the desired protein from the culture medium, e.g., by centrifugation, and assaying the medium (supernatant) for the presence of the desired protein. The presence of LERK-6 in the medium indicates that the protein was secreted from the cells and thus is a soluble form of the desired protein.

Soluble forms of LERK-6 possess many advantages over the native bound LERK-6 protein. Purification of the proteins from recombinant host cells is feasible, since the soluble proteins are secreted from the cells. Further, soluble proteins are generally more suitable for intravenous administration.

Examples of soluble LERK-6 polypeptides include those comprising a substantial portion of the extracellular domain of a native LERK-6 protein. An example of a soluble murine LERK-6 protein comprises amino acids 1–145 of SEQ ID NO:2 and amino acids 1–145 of SEQ ID NO:10. In addition, truncated soluble LERK-6 proteins comprising less than the entire extracellular domain are included in the invention. When initially expressed within a host cell, soluble LERK-6 may additionally comprise one of the heterologous signal peptides described below that is functional within the host cells employed. Alternatively, the protein may comprise the native signal peptide. In one embodiment of the invention, soluble LERK-6 can be expressed as a fusion protein comprising (from N- to C-terminus) the yeast α-factor signal peptide, a FLAG® peptide described below and in U.S. Pat. No. 5,011,912, and soluble LERK-6 consisting of amino acids 1–134 of SEQ ID NO:2 or SEQ ID NO:10. This recombinant fusion protein is expressed in and secreted from yeast cells. The FLAG® peptide facilitates purification of the protein, and subsequently may be cleaved from the soluble LERK-6 using bovine mucosal enterokinase. Isolated DNA sequences encoding soluble LERK-6 proteins are encompassed by the invention.

Truncated LERK-6, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the receptor-binding domain.

As stated above, the invention provides isolated or homogeneous LERK-6 polypeptides, both recombinant and non-recombinant. Variants and derivatives of native LERK-6 proteins that retain the desired biological activity (e.g., the ability to bind hek/elk) may be obtained by mutations of nucleotide sequences coding for native LERK-6 polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

LERK-6 may be modified to create LERK-6 derivatives by forming covalent or aggregative conjugates with other chemical moieties, such as glycosyl groups, lipids, phosphate, acetyl groups and the like. Covalent derivatives of LERK-6 may be prepared by linking the chemical moieties to functional groups on LERK-6 amino acid side chains or at the N-terminus or C-terminus of a LERK-6 polypeptide or the extracellular domain thereof. Other derivatives of LERK-6 within the scope of this invention include covalent or aggregative conjugates of LERK-6 or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a LERK-6 polypeptide. The signal or leader peptide co-translationally or post-translationally directs transfer of the conjugate from its site of synthesis to a site inside or outside of the cell membrane or cell wall.

LERK-6 polypeptide fusions can comprise peptides added to facilitate purification and identification of LERK-6. Such peptides include, for example, poly-His or the antigenic identification peptides described in U.S. Pat. No. 5,011,912 and in Hopp et al., *Bio/Technology* 6:1204, 1988.

The invention further includes LERK-6 polypeptides with or without associated native-pattern glycosylation. LERK-6 expressed in yeast or mammalian expression systems (e.g., COS-7 cells) may be similar to or significantly different from a native LERK-6 polypeptide in molecular weight and glycosylation pattern, depending upon the choice of expression system. Expression of LERK-6 polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the LERK-6 extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The murine LERK-6 and human LERK-6 proteins comprise three such triplets, at amino acids 13–15, 145–147 and 159–161 of SEQ ID NO:2 and SEQ ID NO:10, respectively. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The murine LERK-6 and human LERK-6 contain one KEX2 protease processing site at amino acids 81–82 of SEQ ID NO:2 and SEQ ID NO:10, respectively.

Nucleic acid sequences within the scope of the invention include isolated DNA and RNA sequences that hybridize to the LERK-6 nucleotide sequences disclosed herein under conditions of moderate or severe stringency, and that encode biologically active LERK-6. Conditions of moderate stringency, as defined by Sambrook et al. *Molecular Cloning: A Laboratory Manual*, 2 ed. Vol. 1, pp. 101–104, Cold Spring Harbor Laboratory Press, (1989), include use of a prewashing solution of 5×SSC, 0.5% SDS, 1.0 mM EDTA (pH 8.0) and hybridization conditions of about 55_C, 5×SSC, overnight. Conditions of severe stringency include higher temperatures of hybridization and washing. The skilled artisan will recognize that the temperature and wash solution salt concentration may be adjusted as necessary according to factors such as the length of the nucleic acid molecule.

Due to the known degeneracy of the genetic code wherein more than one codon can encode the same amino acid, a DNA sequence may vary from that shown in SEQ ID NO:1, SEQ ID NO:7, and SEQ ID NO:9 and still encode a LERK-6 protein having the amino acid sequence of SEQ ID NO:2, SEQ ID NO:8, or SEQ ID NO:10, respectively. Such variant DNA sequences may result from silent mutations (e.g., occurring during PCR amplification), or may be the product of deliberate mutagenesis of a native sequence.

The invention provides equivalent isolated DNA sequences encoding biologically active LERK-6, selected from: (a) cDNA comprising the nucleotide sequence presented in SEQ ID NO:1, SEQ ID NO:7, or SEQ ID NO:9; (b) DNA capable of hybridization to a DNA of (a) under moderately stringent conditions and that encodes biologically active LERK-6; and (c) DNA that is degenerate as a result of the genetic code to a DNA defined in (a), or (b) and that encodes biologically active LERK-6. LERK-6 proteins encoded by such DNA equivalent sequences are encompassed by the invention.

DNAs that are equivalents to the DNA sequence of SEQ ID NO:1, and SEQ ID NO:7 or SEQ ID NO:9 will hybridize under moderately and severely stringent conditions to DNA sequences that encode polypeptides comprising amino acids 1–184 of SEQ ID NO:2, SEQ ID NO:8, or amino acids 1–184 of SEQ ID NO:10. Examples of LERK-6 proteins encoded by such DNA, include, but are not limited to, LERK-6 fragments (soluble or GPI-linked) and LERK-6 proteins comprising inactivated N-glycosylation site(s), inactivated KEX2 protease processing site(s), or conservative amino acid substitution(s), as described above. LERK-6 proteins encoded by DNA derived from other mammalian species, wherein the DNA will hybridize to the cDNA of SEQ ID NO:1, SEQ ID NO:7 or SEQ ID NO:9 are also encompassed by the present invention.

Variants possessing the requisite ability to bind hek/elk receptor may be identified by any suitable assay. Biological activity of LERK-6 may be determined, for example, by competition for binding to the ligand binding domain of hek/elk receptor (i.e. competitive binding assays).

One type of a competitive binding assay for a LERK-6 polypeptide uses a radiolabeled, soluble LERK-6 and intact hek/elk-expressing cells. Instead of intact cells, one could substitute soluble hek/elk:Fc fusion proteins (such as a hek:Fc or elk:Fc fusion protein) bound to a solid phase through the interaction of a Protein A, Protein G or an antibody to the hek, elk or Fc portions of the molecule, with the Fc region of the fusion protein. Another type of competitive binding assay utilizes radiolabeled soluble hek or elk receptors such as a hek:Fc or elk:Fc fusion protein, and intact cells expressing LERK-6.

Competitive binding assays can be performed following conventional methodology. For example, radiolabeled LERK-6 can be used to compete with a putative LERK-6 homolog to assay for binding activity against surface-bound hek/elk. Qualitative results can be obtained by competitive autoradiographic plate binding assays, or Scatchard plots may be utilized to generate quantitative results.

Alternatively, hek/elk-binding proteins, such as LERK-6 and anti-hek/elk antibodies, can be bound to a solid phase such as a column chromatography matrix or a similar substrate suitable for identifying, separating or purifying cells that express hek/elk on their surface. Binding of a hek/elk-binding protein to a solid phase contacting surface can be accomplished by any means, for example, by constructing a LERK-6:Fc fusion protein and binding such to the solid phase through the interaction of Protein A or Protein G. Various other means for fixing proteins to a solid phase are well known in the art and are suitable for use in the present invention. For example, magnetic microspheres can be coated with LERK-6 and held in the incubation vessel through a magnetic field. Suspensions of cell mixtures containing hek/elk-expressing cells are contacted with the solid phase that has LERK-6 polypeptides thereon. Cells having hek/elk on their surface bind to the fixed LERK-6 and unbound cells then are washed away. This affinity-binding method is useful for purifying, screening or separating such hek/elk-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of hek/elk:LERK-6 interactions, the enzyme preferably would cleave the hek/elk receptor, thereby freeing the resulting cell suspension from the "foreign" LERK-6 material. The purified cell population, especially if obtained from fetal tissue, then may be used to repopulate mature (adult) tissues. For example, such purified neural cells can be administered to a patient having a neurodegenerative disorder such as Parkinson's disease, Alzheiner's disease, Lou Gehrig's disease, etc.

Alternatively, mixtures of cells suspected of containing hek/elk$^+$ cells first can be incubated with biotinylated LERK-6. Incubation periods are typically at least one hour in duration to ensure sufficient binding to hek/elk The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.*, 10D:239 (1986). Wash of unbound material and the release of the bound cells is performed using conventional methods.

As described above, LERK-6 can be used to separate cells expressing hek/elk. In an alternative method, LERK-6 or an extracellular domain or a fragment thereof can be conjugated to a detectable moiety such as $^{125}$I to detect hek/elk-expressing cells. Radiolabeling with $^{125}$I can be performed by any of several standard methodologies that yield a functional $^{125}$I-LERK-6 molecule labeled to high specific activity. Or an iodinated or biotinylated antibody against the hek/elk region or the Fc region of the molecule could be used. Another detectable moiety such as an enzyme that can catalyze a colorimetric or fluorometric reaction, biotin or avidin may be used. Cells to be tested for hek/elk-expression can be contacted with labeled LERK-6. After incubation, unbound labeled LERK-6 is removed and binding is measured using the detectable moiety.

The binding characteristics of LERK-6 (including variants) may also be determined using the conjugated, soluble hek/elk (for example, $^{125}$I-hek/elk:Fc) in competition assays similar to those described above. In this case, however, intact cells expressing hek/elk bound to a solid substrate, are used to measure the extent to which a sample containing a putative LERK-6 variant competes for binding with a conjugated a soluble hek/elk to LERK-6.

Other means of assaying for LERK-6 include the use of anti-LERK-6 antibodies, cell lines that proliferate in response to LERK-6, or recombinant cell lines that express hek/elk and proliferate in the presence of LERK-6.

The LERK-6 proteins disclosed herein also may be employed to measure the biological activity of elk or hek proteins in terms of their binding affinity for LERK-6. As one example, LERK-6 may be used in determining whether biological activity is retained after modification of an elk or hek protein (e.g., chemical modification, truncation, mutation, etc.). The biological activity of an elk or hek protein thus can be ascertained before it is used in a research study, or possibly in the clinic, for example.

LERK-6 proteins find use as reagents that may be employed by those conducting "quality assurance" studies, e.g., to monitor shelf life and stability of elk protein under different conditions. To illustrate, LERK-6 may be employed in a binding affinity study to measure the biological activity of an elk protein that has been stored at different temperatures, or produced in different cell types. The binding affinity of the modified elk protein for LERK-6 is compared to that of an unmodified elk protein to detect any adverse impact of the modifications on biological activity of elk. Likewise, the biological activity of a hek protein can be assessed using LERK-6.

LERK-6 polypeptides also find use as carriers for delivering agents attached thereto to cells bearing the elk or hek cell surface receptor. Expression of hek antigen has been reported for certain leukemic cell lines, including the human T-cell leukemia cell line designated JM and the human pre-B cell leukemia cell line designated LK63 (Boyd et al., *J. Biol. Chem.* 267:3262, 1992, and Wicks et al., *Proc. Nati. Acad. Sci. USA,* 89:1611, 1992). LERK-6 proteins thus can be used to deliver diagnostic or therapeutic agents to these cells (or to other cell types found to express hek on the cell surface) in in vitro or in vivo procedures.

One example of such use is to expose a hek$^+$ or elk$^+$ leukemic cell line to a therapeutic agent/LERK-6 conjugate to assess whether the agent exhibits cytotoxicity toward the leukemic cells. A number of different therapeutic agents attached to LERK-6 may be included in an assay to detect and compare the cytotoxic effect of the agents on the leukemic cells. LERK-6/diagnostic agent conjugates may be employed to detect the presence of hek$^+$ cells in vitro or in vivo.

Diagnostic and therapeutic agents that may be attached to a LERK-6 polypeptide include, but are not limited to, drugs, toxins, radionuclides, chromophores, enzymes that catalyze a calorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the LERK-6 by any suitable conventional procedure. LERK-6, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to LERK-6 by using a suitable bifunctional chelating agent, for example.

Conjugates comprising LERK-6 and a suitable diagnostic or therapeutic agent (preferably covalently linked) are thus prepared. The conjugates are administered or otherwise employed in an amount appropriate for the particular application.

Another use of the LERK-6 of the present invention is as a research tool for studying the role that LERK-6, in conjunction with elk or hek, may play in growth or differentiation of cells bearing the elk or hek receptor. The LERK-6 polypeptides of the present invention also may be employed in in vitro assays for detection of elk or LERK-6 or the interactions thereof. Likewise, LERK-6 finds use in assays for hek or the interaction of LERK-6 with hek.

As discussed above, when various rat tissues were analyzed for elk mRNA, transcripts were detected only in brain and testis (Lhotak et al., supra). Binding of LERK-6 to eph-related receptors on neural tissue is believed to exert a neuroprotective or neurotrophic effect.

LERK-6 finds use as a tissue culture reagent. A LERK-6 protein can be added to neurons cultured in vitro to enhance the viability or prolong the lifespan of the cultured neurons, thus facilitating research studies, and possible clinical treatment of neural tissue.

One embodiment of the present invention is directed to a method of treating disorders of neural tissue, involving contacting the neural tissue with LERK-6. Such disorders include injury or neurologic diseases, either chronic or acute. A LERK-6 protein may be administered to a mammal to treat such an injury or disease. In one embodiment of the invention, LERK-6 is employed in treating neurodegenerative conditions characterized or mediated, at least in part, by the mechanism of neural death known as excitotoxicity. In addition, LERK-6 may be administered to a mammal to exert a trophic effect on neural tissue. In a patient suffering loss of or damage to neurons due to injury or disease, LERK-6 may enhance the viability of those neurons that have survived.

LERK-6 polypeptides of the invention can be formulated according to known methods used to prepare pharmaceutically useful compositions. LERK-6 can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain LERK-6 complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of LERK-6. LERK-6 can also be conjugated to antibodies against tissue-specific receptors, ligands or antigens, or coupled to ligands of tissue-specific receptors. Where hek/elk is found on neoplastic cells, the LERK-6 may be conjugated to a toxin whereby LERK-6 is used to deliver the toxin to the specific site, or may be used to sensitize such neoplastic cells to subsequently administered anti-neoplastic agents.

LERK-6 can be administered topically, parenterally, or by inhalation. The term "parenteral" includes subcutaneous injections, intravenous, intramuscular, intracisternal injection, or infusion techniques. These compositions will typically contain an effective amount of the LERK-6, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

LERK-6 polypeptides may exist as oligomers, such as covalently-linked or non-covalently-linked dimers or trimers. Oligomers may be linked by disulfide bonds formed between cysteine residues on different LERK-6 polypeptides. In one embodiment of the invention, a LERK-6 dimer is created by fusing LERK-6 to the Fc region of an antibody (e.g., IgG1) in a manner that does not interfere with binding of LERK-6 to the hek/elk ligand-binding domain. The Fc polypeptide preferably is fused to the C-terminus of a soluble LERK-6 (comprising only the receptor-binding). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the LERK-6:Fc fusion protein is inserted into an appropriate expression vector. LERK-6:Fc fusion proteins are allowed to assemble much like antibody molecules, whereupon interchain disulfide bonds form between Fc polypeptides, yielding divalent LERK-6. If fusion proteins are made with both heavy and light chains of an antibody, it is possible to form a LERK-6 oligomer with as many as four LERK-6 extracellular regions. Alternatively, one can link two soluble LERK-6 domains with a peptide linker.

Suitable host cells for expression of LERK-6 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce LERK-6 polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium,* and various other species within the genera Pseudomonas, Streptomyces, and Staphylococcus. In a prokaryotic host cell, such as *E. coli*, a LERK-6 polypeptide may include an N-terminal methionine residue to facilitate expression of the recombinant polypeptide in the prokaryotic host cell. The N-terminal Met may be cleaved from the expressed recombinant LERK-6 polypeptide.

LERK-6 polypeptides may be expressed in yeast host cells, preferably from the Saccharomzyces genus (e.g., *S. cerevisiae*). Other genera of yeast, such as Pichia, *K. lactis* or Kluyveromyces, may also be employed. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the LERK-6 polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U. S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant LERK-6 polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Inmunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No.07/701,415, filed May 16, 1991, incorporated by reference herein. The vectors may be derived from retroviruses. In place of the native signal sequence, and in addition to an intiator methionine, a heterologous signal sequence may be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

LERK-6 as an isolated, purified or homogeneous protein according to the invention may be produced by recombinant expression systems as described above or purified from naturally occurring cells. LERK-6 can be purified to substantial homogeneity, as indicated by a single protein band upon analysis by SDS-polyacrylamide gel electrophoresis (SDS-PAGE).

One process for producing LERK-6 comprises culturing a host cell transformed with an expression vector comprising a DNA sequence that encodes LERK-6 under conditions sufficient to promote expression of LERK-6. LERK-6 is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify LERK-6. Some or all of the foregoing purification steps, in various combinations, are well known and can be employed to provide a substantially homogeneous recombinant protein.

It is possible to utilize an affinity column comprising the ligand-binding domain of hek/elk receptors to affinity-purify expressed LERK-6 polypeptides. LERK-6 polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds LERK-6. Example 5 describes a procedure for employing LERK-6 of the invention to generate monoclonal antibodies directed against LERK-6.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps.

Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express LERK-6 as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Useful fragments of the LERK-6 nucleic acids include antisense or sense oligonucleotides comprising a single-stranded nucleic acid sequence (either RNA or DNA) capable of binding to target LERK-6 mRNA (sense) or LERK-6 DNA (antisense) sequences. Antisense or sense oligonucleotides, according to the present invention, comprise a fragment of the coding region of LERK-6 cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of LERK-6 proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In addition to the above, the following examples are provided to illustrate particular embodiments and not to limit the scope of the invention.

EXAMPLE 1

Cloning of Murine LERK-6 cDNA

This example describes a procedure for isolating a DNA sequence encoding murine LERK-6 of the invention. A commercially available 11.5 day murine embryonic cDNA library was obtained from Clonetech Laboratories, Inc., Palo Alto, Calif. The library was plated according to the procedures detailed in the manual provided by Clonetech, and screened using the $^{32}$P-radiolabelled probes. The probes each were generated using standard techniques. Generally, polymerase chain reaction (PCR) (Mullis and Faloona, *Meth. Enzymol.* 155:335–350, 1987) amplifications were performed using two sets of primers. The first set,

| GATATTTACT GCCCGCACTA CAACAGCT | SEQ ID NO:3 |
|---|---|
| AGAGAAGGCG CTGTAGCGCT GGAAC | SEQ ID NO:4 | was used to generate amplified double stranded DNA fragments from the DNA of LERK-3. LERK-3 is the subject of copending patent application Ser. Nos. 08/109,745; 08/114,426, 08/161,132 and 08/240,124 filed May 9, 1994. The probe from LERK-3 comprised nucleotides 260 through 481 of the SEQ ID NO:1 of copending application Ser. No. 08/240,124 filed May 9, 1994. The second set of primers,

| ACGTAGTCTA CTGGAACTCC AGTAAC CCCA G | SEQ ID NO:5 |
|---|---|
| AGCCTCAAGC ACTGGCCAGA ACTCTC TCTG GAGT | SEQ ID NO:6 | was used to generate amplified double stranded DNA fragments from the DNA of LERK-4. LERK-4 also is the subject of copending patent application Ser. Nos. 08/109,745; 08/114,426, 08/161,132 and 08/240,124 filed May 9, 1994. The probe from LERK-3 comprised nucleotides 110 through 467 of the SEQ ID NO:3 of copending application Ser. No. 08/240,124 filed May 9, 1994. The fragments were radio-labelled with $^{32}$p, and used as probes to screen a murine embryonic library.

Screening with the probes was conducted by conventional procedures, and hybridizing clones were identified. The hybridizing conditions consisted of 42° C. and 50% Starks washed to 0.1×SSC at 63° C. The nucleotide sequence of the cDNA insert of one individual clone isolated from the murine embryonic library, designated clone λ13, was determined. A substantially complete cDNA sequence of the coding region of the clone λ13 cDNA, and the amino acid sequence encoded thereby, are presented in SEQ ID NO:1 and SEQ ID NO:2, respectively. The open-reading frame within this sequence encodes a protein of 184 amino acids. Since the N-termini of the proteins of the LERK family are non-homologous, it is believed that the first amino acid of SEQ ID NO:1 (Ala) is located at or very near the native N-terminus. In addition, because LERK-6 of this invention is homologous with other biologically active LERK molecules, there is a significant probability that the cDNA of SEQ ID NO:1 encodes a biologically active protein. Secretion of such active protein is possible through the procedures described above with respect to addition of a suitable initiator methionine and a suitable signal sequence, such as that for murine IL-7. The amino acid sequence of LERK-6 is 58% homologous to that of a cytokine termed LERK-3.

A cell lysate containing clone λ13 DNA (the LERK-6 cDNA in λgt10) was deposited with the American Type Culture Collection, Rockville, Md., USA on Jul. 15, 1994, and assigned accession number ATCC 75829. The deposit was made under the terms of the Budapest Treaty.

EXAMPLE 2

Cloning of Human LERK-6

This example describes the cloning of nucleic acids encoding human LERK-6. Human LERK-6 sequence is from a genomic clone isolated by probing a human genomic library with a murine LERK-6 cDNA probe encoding amino acids 30–173. Plaque containing filters were hybridized to $^{32}$P-labeled probe at 55° C. for 24 h, washed to 0.5×SSC at 55° C., and exposed to X-ray film (Kodak XAR-5). A sequence of nucleic acids contained in such clone is shown below, also in SEQ ID NO:7, and the amino acids encoded thereby are shown in SEQ ID NO:8:

exposed to X-ray film. Two different clones were isolated using this technique. Then the same isolation process was repeated using the human genomic DNA library from a different preparation (Stratagene, La Jolla, Calif.). This process resulted in the isolation of a third clone having a different nucleotide sequence. The three isolated clones were restriction mapped and then subcloned into bluescript plasmid and sequenced. Using the murine LERK-6 sequence as a template the introns and exons of the clones were identified. The full length human LERK-6 encoding DNA sequence as determined by comparing the coding regions of the murine LERK-6 is identified in SEQ ID NO:9 and the amino acid sequence encoded by the full length DNA sequence is identified in SEQ ID NO:10.

Plasmids including the cloned LERK-6 DNA were deposited with the American Type Culture Collection, Rockville, Md., USA on August ___1997, and assigned accession number ATCC____. The deposit was made under the terms of the Budapest Treaty.

EXAMPLE 3

Preparation of Soluble elk:Fc Fusion Protein

This example describes construction of an expression vector encoding a soluble elk:Fc fusion protein. This fusion protein can be employed in the binding assays of Example 5, to determine the binding characteristics of LERK-6.

A DNA and encoded amino acid sequence for rat elk cDNA is presented in Lhotak et al. (*Mol. Cell. Biol.* 11:2496, 1991), hereby incorporated by reference. The rat elk protein has a 538 amino acid extracellular domain, a 25 amino acid transmembrane domain, and a 419 amino acid cytoplasmic domain.

A rat elk cDNA fragment was fused to the 5′ end of cDNA encoding the Fc portion of a human IgG1 antibody. The rat

```
G TTC CAC GCA GGC GCG GGG GAC GAC GGC GGG GGC TAC ACG GTG GAG      46
  Phe His Ala Gly Ala Gly Asp Asp Gly Gly Gly Tyr Thr Val Glu
  1               5                   10                  15

GTG AGC ATC AAT GAC TAC CTG GAC ATC TAC TGC CCG CAC TAT GGG GCG    94
Val Ser Ile Asn Asp Tyr Leu Asp Ile Tyr Cys Pro His Tyr Gly Ala
                20                  25                  30

CCG CTG CCG CCG GCC GAG CGC ATG GAG CAC TAC GTG CTG TAC ATG GTC   142
Pro Leu Pro Pro Ala Glu Arg Met Glu His Tyr Val Leu Tyr Met Val
            35                  40                  45

AAC GGC GAG GGC CAC GCC TCC TGC GAC CAC CGC CAG CGC GGC TTC AAG   190
Asn Gly Glu Gly His Ala Ser Cys Asp His Arg Gln Arg Gly Phe Lys
        50                  55                  60

CGC TGG GAG TGC AAC CGG CCC GCG GCG CCC GGG GGG CCG CTC AAG TTC   238
Arg Trp Glu Cys Asn Arg Pro Ala Ala Pro Gly Gly Pro Leu Lys Phe
    65                  70                  75

TCG GAG AAG TTC CAG CTC TTC ACG CCC TTC TCC CTG GGC TTC GAG TTC   286
Ser Glu Lys Phe Gln Leu Phe Thr Pro Phe Ser Leu Gly Phe Glu Phe
80                  85                  90                  95

CGG CCC GGC CAC GAG TAT TAC TAC ATC T                             314
Arg Pro Gly His Glu Tyr Tyr Tyr Ile
                100
```

Compared to murine LERK-6, human LERK-6 possesses a 98.077 percent similarity and 93.269 percent identity.

A complete human LERK-6 DNA was isolated by probing a human genomic DNA library (Stratagene, La Jolla, Calif.) with the nucleic acid sequence shown in SEQ ID NO:7. Plague containing filters were hybridized to the $^{32}$P-labeled probe at 55° C. for 24 h, washed to 0.5×SSC at 55° C., and elk cDNA can be obtained from T. Pawson (Samuel Lunenfeld Research Institute, Mt. Sinai Hospital, Toronto). An Asp718 restriction endonuclease cleavage site was introduced upstream of the elk coding region. An Asp 718-BglII fragment of rat elk cDNA (comprising the entire extracellular domain, the transmembrane region, and a small portion of the cytoplasmic domain) was isolated.

DNA encoding a single polypeptide chain comprising the Fc region of a human IgG1 antibody was cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. The nucleotide sequence of the cloned DNA, along with the amino acid sequence of the Fc polypeptide encoded thereby, are described in PCT application WO 93/10151, hereby incorporated by reference. A unique BglII site has been introduced, and encompasses the codons for amino acids three and four of the Fc polypeptide. The encoded Fc polypeptide extends from the N-terminal hinge region to the native C-terminus, i.e., is an essentially full-length antibody Fc region.

The above-described Asp718-BglII elk cDNA fragment was cloned into the pBLUESCRIPT SK® vector containing the Fc cDNA, such that the elk cDNA is positioned upstream of the Fc cDNA. Single stranded DNA derived from the resulting gene fusion was mutagenized by the method described in Kunkel (*Proc. Natl. Acad. Sci. USA* 82:488, 1985) and Kunkel et al. (*Methods in Enzymol.* 154:367, 1987) in order to perfectly fuse the entire extracellular domain of elk to the Fc sequence. The mutagenized DNA was sequenced to confirm that the proper nucleotides had been removed (i.e., that the transmembrane region and partial cytoplasmic domain DNA were deleted) and that the elk and Fc sequences were in the same reading frame.

The elk:Fc fusion protein preferably is synthesized in mammalian host cells, such as CV1-EBNA or COS-7 cells. The elk:Fc gene fusion was excised and inserted into a mammalian expression vector designated HAV-EO (Dower et al., *J. Immunol.* 142:4314, 1989). Mammalian host cells were transfected with the resulting recombinant expression vector and cultivated to allow transient expression of the fusion protein, which was secreted into the culture medium via the elk signal peptide. The elk:Fc fusion protein was purified by affinity chromatography, using a protein A sepharose column.

EXAMPLE 4

Preparation of Soluble hek:Fc Fusion Protein

This example describes construction of an expression vector encoding a soluble hek:Fc fusion protein. This fusion protein can be employed in the binding assays of Example 5, to determine the binding characteristics of LERK-6.

A DNA and encoded amino acid sequence for human hek cDNA is presented in Wicks et al. (*Proc. Natl. Acad. Sci. USA*, 89:1611, 1992), incorporated herein by reference. This hek protein comprises (from N- to C-terminus) an extracellular domain, a transmembrane domain, and a cytoplasmic domain.

Two DNA fragments, one encoding an N-terminal fragment of the extracellular domain of hek and the other encoding a C-terminal fragment of the hek extracellular domain, were isolated by polymerase chain reactions (PCR) conducted under standard conditions, using oligonucleotide primers based on the hek nucleotide sequence published by Wicks et al., supra. The template for the PCR was cDNA prepared from MRNA isolated from a human T-cell leukemic cell line designated CCRF-HSB-2 (ATCC CCL-120.1). The PCR products containing the 5' end of the hek DNA were digested with SpeI and HindIII to isolate a DNA fragment extending from the 5' end of the mature human hek sequence (i.e., lacking DNA encoding the signal sequence) to a HindIII site found in the hek gene. The PCR products containing the 3' end of the hek extracellular domain DNA were digested with HindIII and ClaI to isolate a fragment extending from the internal HindIII site to a ClaI site just downstream of the 3' end of the sequence encoding the hek extracellular domain. The ClaI site is in a multiple cloning site (mcs) introduced just downstream of the extracellular domain.

DNA encoding a mutein of the Fc region of a human IgG1 antibody was isolated. This Fc mutein DNA and the polypeptide encoded thereby are described in U.S. patent application Ser. No. 08/097,827, entitled "Novel Cytokine Which is a Ligand for OX40" filed Jul. 23, 1993, which application is incorporated herein by reference. The mutein DNA was derived from a native Fc polypeptide-encoding DNA by site-directed mutagenesis conducted essentially as described by Deng and Nickoloff, *Anal. Biochem.* 200:81 (1992). The amino acid sequence of the Fc mutein polypeptide is identical to that of the native Fc polypeptide described in PCT application WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

A recombinant vector containing the Fc mutein DNA was cleaved with ClaI and NotI, which cleave the vector in a polylinker region immediately upstream and downstream, respectively, of the Fc mutein DNA insert. The desired Fc mutein-encoding fragment was isolated.

The mutein Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate hek:Fc fusion proteins, creating dimers.

A mammalian expression vector designated SMAG4 was cleaved with SpeI and NotI. The SMAG4 vector comprises a murine interleukin-7 signal peptide-encoding sequence (described in U.S. Pat. No. 4,965,195) inserted into the mammalian high expression vector pDC201 (described in Sims et al., *Science* 241:585, 1988, and in PCT application WO 89/03884), which is also capable of replication in *E. coli*. SpeI cleaves the vector immediately downstream of the IL-7 signal peptide-encoding sequence. NotI cleaves approximately 155 bp downstream of the SpeI site in a multiple cloning site of the vector. The large SpeI/NotI fragment containing the vector sequences and the IL-7 signal peptide-encoding DNA was isolated.

A four-way ligation was conducted to insert the two hek-encoding DNA fragments and the Fc mutein-encoding DNA fragment described above into the SpeI/NotI cleaved SMAG4 expression vector. *E. coli* cells were transfected with the ligation mixture and the desired recombinant vector was isolated therefrom. The isolated vector encodes a fusion protein comprising (from N- to C-terminus) the murine IL-7 signal peptide, the hek extracellular domain, four amino acids encoded by the introduced mcs, and the Fc mutein.

The expression vector was then co-transfected with plasmid pSV3.NEO into CV1/EBNA cells. The CV1/EBNA cell line (ATCC CRL 10478) was derived from a monkey kidney cell line as described in McMahan et al. (*EMBO J.*, 10:2821, 1991). Vector pSV3.NEO expresses SV40 T-antigen, which is not produced by the host cells. The pSV3.NEO vector is similar to pSV3 (Mulligan and Berg, *Proc. Natl. Acad. Sci. USA* 78:2072, 1981), but additionally contains a neomycin resistance gene. The transformed cells were cultivated to allow transient expression of the fusion protein, which is secreted into the culture medium via the murine IL-7 signal peptide. The fusion protein can be purified on a protein A Sepharose column, eluted, and used to screen cells for the ability to bind the hek:Fc protein or elk:Fc protein.

EXAMPLE 5

Binding Study

The ability of LERK-6 to bind to elk or hek can be determined by using the following assay. Cells expressing LERK-6 on the cell surface are prepared. LERK-6 DNA is amplified by PCR. The primers employed in the PCR are selected to define the termini of the coding region of the LERK-6 DNA, and also include a Xho I restriction site at the 5' end and a Not I site at the 3' end of the amplified DNA. The 5' primer additionally included a consensus Kozak sequence upstream of the initiation codon.

The reaction products are digested with Xho I and Not I and inserted into an expression vector cleaved with Sal I (which is compatible with Xho I) and Not I. The expression vector can be pDC410, which is a mammalian expression vector that also replicates in *E. coli*. pDC410 is similar to pDC406 (McMahan et al., *EMBO J.* 10:2821, 1991). The pDC410 multiple cloning site (mcs) differs from that of pDC406 in that it contains additional restriction sites and three stop codons (one in each reading frame). A T7 polymerase promoter downstream of the mcs facilitates sequencing of DNA inserted into the mcs. In addition, the EBV origin of replication is replaced by DNA encoding the SV40 large T antigen (driven from an SV40 promoter) in pDC410.

CV1-EBNA-1 cells in 10 $cm^2$ dishes are transfected with the recombinant expression vector containing LERK-6 DNA. The CV-1/EBNA-1 cell line (ATCC CRL 10478) constitutively expresses EBV nuclear antigen-1 driven from the CMV immediate-early enhancer/promoter. CV1-EBNA-1 is derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, a binding assay is conducted by the following procedure. The transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37_C with various concentrations of the elk:Fc fusion protein prepared in Example 2 or the hek:Fc fusion protein prepared in Example 3. Cells then are washed and incubated with a constant saturating concentration of a $^{125}$I-mouse anti-human IgG in binding medium, with gentle agitation for 1 hour at 37_C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any elk:Fc or hek:Fc fusion protein that has bound to the cells. In all assays, non-specific binding of $^{125}$I-antibody is assayed in the absence of elk:Fc (or hek:Fc), as well as in the presence of elk:Fc (or hek:Fc) and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

EXAMPLE 6

Monoclonal Antibodies to LERK-6

This example illustrates a method for preparing monoclonal antibodies to LERK-6. Purified LERK-6, a fragment thereof such as the extracellular domain, synthetic peptides or cells that express LERK-6 can be used to generate monoclonal antibodies against LERK-6 using conventional techniques, for example, those techniques described in U.S. Pat. No. 4,411,993. Briefly, mice are immunized with LERK-6 as an immunogen emulsified in complete Freund's adjuvant, and injected in amounts ranging from 10–100 µg subcutaneously or intraperitoneally. Ten to twelve days later, the immunized animals are boosted with additional LERK-6 emulsified in incomplete Freund's adjuvant. Mice are periodically boosted thereafter on a weekly to bi-weekly immunization schedule. Serum samples are periodically taken by retro-orbital bleeding or tail-tip excision to test for LERK-6 antibodies by dot blot assay, ELISA (Enzyme-Linked Immunosorbent Assay) or inhibition of hek or elk binding.

Following detection of an appropriate antibody titer, positive animals are provided one last intravenous injection of LERK-6 in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified LERK-6 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-LERK-6-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to LERK-6.

EXAMPLE 7

Generation of Transgenic Mice That Overexpress LERK-6

This example describes a procedure for generating transgenic mice that overexpress LERK-6. LERK-6-overexpressing transgenic mice can be studied to determine the biological effects of overexpression. Mouse (B16/J) pronuclei are microinjected with LERK-6 DNA according to the method described by Gordon et al., *Science* 214:1244–1246, (1981). In general, fertilized mouse eggs having visible pronuclei are first placed on an injection chamber and held in place with a small pipet. An injection pipet is used to inject the gene encoding the LERK-6 (e.g., clone #6C) into the pronuclei of the egg. Injected eggs are either (i) transferred into the oviduct of a 0.5 day p.c. pseudopregnant female; (ii) cultured in vitro to the two-cell stage (overnight) and transferred into the oviduct of a 0.5 day p.c. pseudopregnant female; or (iii) cultured in vitro to the blastocyst stage and transferred into the uterus of a 2.5 day p.c. pseudopregnant female. Preferably, either of the first two options can be used since they avoid extended in vitro culture, and preferably, approximately 20–30 microinjected eggs should be transferred to avoid small litters.

---

What is claimed is:

1. An isolated DNA molecule encoding a LERK-6 polypeptide that binds hek/elk, wherein said polypeptide consists of amino acids 1 to 104 of SEQ ID NO:8.

2. An isolated DNA molecule encoding a LERK-6 polypeptide that binds hek/elk, wherein said polypeptide consists of amino acids 1 to 184 of SEQ ID NO:10.

3. An isolated DNA molecule encoding a LERK-6 polypeptide that binds hek/elk, wherein said polypeptide consists of amino acids 1 to 145 of SEQ ID NO:10.

4. An isolated DNA molecule encoding a LERK-6 polypeptide that binds hek/elk, wherein said polypeptide consists of amino acids 1 to 134 of SEQ ID NO:10.

5. The isolated DNA molecule of claim 1, wherein said DNA molecule consists of nucleotides 2 to 313 of SEQ ID NO:7.

6. The isolated DNA molecule of claim 2, wherein said DNA molecule consists of nucleotides 88 to 642 of SEQ ID NO:9.

7. The isolated DNA molecule of claim 3, wherein said DNA molecule consists of nucleotides 88 to 522 of SEQ ID NO:9.

8. The isolated DNA molecule of claim 4, wherein said DNA molecule consists of nucleotides 88 to 489 of SEQ ID NO:9.

9. An expression vector comprising a DNA molecule of claim 1.

10. An expression vector comprising a DNA molecule of claim 2.

11. An expression vector comprising a DNA molecule of claim 3.

12. An expression vector comprising a DNA molecule of claim 4.

13. An expression vector comprising a DNA molecule of claim 5.

14. An expression vector comprising a DNA molecule of claim 6.

15. An expression vector comprising a DNA molecule of claim 7.

16. An expression vector comprising a DNA molecule of claim 8.

17. A host cell transformed or transfected with a expression vector of claim 9.

18. A host cell transformed or transfected with a expression vector of claim 10.

19. A host cell transformed or transfected with a expression vector of claim 11.

20. A host cell transformed or transfected with a expression vector of claim 12.

21. A host cell transformed or transfected with a expression vector of claim 13.

22. A host cell transformed or transfected with a expression vector of claim 14.

23. A host cell transformed or transfected with a expression vector of claim 15.

24. A host cell transformed or transfected with a expression vector of claim 16.

25. A process for preparing a LERK-6 polypeptide, comprising culturing a host cell of claim 17 under conditions promoting expression of LERK-6 polypeptide, and recovering the LERK-6 polypeptide so expressed.

26. A process for preparing a LERK-6 polypeptide, comprising culturing a host cell of claim 18 under conditions promoting expression of LERK-6 polypeptide, and recovering the LERK-6 polypeptide so expressed.

27. A process for preparing a LERK-6 polypeptide, comprising culturing a host cell of claim 19 under conditions promoting expression of LERK-6 polypeptide, and recovering the LERK-6 polypeptide so expressed.

28. A process for preparing a LERK-6 polypeptide, comprising culturing a host cell of claim 20 under conditions promoting expression of LERK-6 polypeptide, and recovering the LERK-6 polypeptide so expressed.

29. A process for preparing a LERK-6 polypeptide, comprising culturing a host cell of claim 21 under conditions promoting expression of LERK-6 polypeptide, and recovering the LERK-6 polypeptide so expressed.

30. A process for preparing a LERK-6 polypeptide, comprising culturing a host cell of claim 12 under conditions promoting expression of LERK-6 polypeptide, and recovering the LERK-6 polypeptide so expressed.

31. A process for preparing a LERK-6 polypeptide, comprising culturing a host cell of claim 23 under conditions promoting expression of LERK-6 polypeptide, and recovering the LERK-6 polypeptide so expressed.

32. A process for preparing a LERK-6 polypeptide, comprising culturing a host cell of claim 24 under conditions promoting expression of LERK-6 polypeptide, and recovering the LERK-6 polypeptide so expressed.

* * * * *